(12) United States Patent
Burbank et al.

(10) Patent No.: US 7,651,511 B2
(45) Date of Patent: Jan. 26, 2010

(54) VASCULAR CLAMP FOR CAESARIAN SECTION

(75) Inventors: Fred H. Burbank, Laguna Niguel, CA (US); Michael L. Jones, San Clemente, CA (US); R. J. Serra, Irvine, CA (US); Greig E. Altieri, Laguna Beach, CA (US); Jill Uyeno, Irvine, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 731 days.

(21) Appl. No.: 10/359,386

(22) Filed: Feb. 5, 2003

(65) Prior Publication Data

US 2005/0101974 A1    May 12, 2005

(51) Int. Cl.
    *A61B 17/08*    (2006.01)
(52) U.S. Cl. ..................................... 606/158
(58) Field of Classification Search ............ 606/157, 606/158, 205–207, 119; 81/421–424; 269/259, 269/261, 263; 24/507, 521
    See application file for complete search history.

(56) References Cited

U.S. PATENT DOCUMENTS

| | | | | |
|---|---|---|---|---|
| 3,209,753 | A | * | 10/1965 | Hawkins et al. ............. 606/207 |
| 3,411,505 | A | | 11/1968 | Nobis |
| 3,777,740 | A | * | 12/1973 | Hokanson ................... 600/455 |
| 3,779,248 | A | * | 12/1973 | Karman ....................... 606/207 |
| 4,120,302 | A | | 10/1978 | Ziegler |
| 4,226,240 | A | | 10/1980 | Walker, Jr. |
| 4,292,960 | A | | 10/1981 | Paglione |
| 4,428,374 | A | | 1/1984 | Auburn |
| 4,428,379 | A | | 1/1984 | Robbins et al. |
| 4,509,528 | A | * | 4/1985 | Sahota ........................ 600/504 |

(Continued)

FOREIGN PATENT DOCUMENTS

DE       195 28 440 A      2/1997

(Continued)

OTHER PUBLICATIONS

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

(Continued)

*Primary Examiner*—Todd E Manahan
*Assistant Examiner*—Lindsey Bachman

(57) ABSTRACT

The invention provides devices, systems and methods for clamping arteries which are useful in reducing or abolishing blood flow in an artery, and may be used to control hemorrhage following a caesarian delivery. A clamping device embodying features of the invention includes a pair of clamping members with opposed pressure-applying members having facing pressure-applying surfaces, at least one of which is a yieldable pressure-applying surface. The yieldable pressure-applying surface is preferably resilient. The clamping members are configured to adjust the distance between pressure-applying surfaces, and a blood flow sensor is disposed on at least one of the pressure-applying members to aid in locating the target artery and also to monitor blood flow through the artery. The clamping device is particularly suitable for occluding uterine arteries by compressing the broad ligament which contains the uterine artery and which is connected to the patient's uterus with the arterial clamp.

27 Claims, 4 Drawing Sheets

U.S. PATENT DOCUMENTS

| | | | |
|---|---|---|---|
| 4,650,466 A | | 3/1987 | Luther |
| 4,757,823 A | * | 7/1988 | Hofmeister et al. .......... 600/437 |
| 4,821,719 A | * | 4/1989 | Fogarty ...................... 606/158 |
| 4,945,896 A | | 8/1990 | Gade |
| 4,991,588 A | | 2/1991 | Pflueger et al. |
| 4,994,069 A | | 2/1991 | Ritchart et al. |
| 5,037,430 A | | 8/1991 | Hasson |
| 5,037,433 A | | 8/1991 | Wilk et al. |
| 5,081,997 A | | 1/1992 | Bosley, Jr. et al. |
| 5,108,408 A | * | 4/1992 | Lally .......................... 606/119 |
| 5,201,314 A | | 4/1993 | Bosley et al. |
| 5,226,911 A | | 7/1993 | Chee et al. |
| 5,261,409 A | | 11/1993 | Dardel |
| 5,275,166 A | | 1/1994 | Vaitenkunas et al. |
| 5,277,181 A | * | 1/1994 | Mendelson et al. ......... 600/322 |
| 5,289,831 A | | 3/1994 | Bosley |
| 5,336,229 A | | 8/1994 | Noda |
| 5,336,231 A | | 8/1994 | Adair |
| 5,383,922 A | | 1/1995 | Zipes et al. |
| 5,427,108 A | | 6/1995 | Bollinger |
| 5,456,693 A | | 10/1995 | Conston et al. |
| 5,458,596 A | | 10/1995 | Lax et al. |
| 5,488,958 A | | 2/1996 | Topel et al. |
| 5,496,331 A | | 3/1996 | Xu et al. |
| 5,507,744 A | | 4/1996 | Tay et al. |
| 5,542,944 A | | 8/1996 | Bhatta |
| 5,549,624 A | | 8/1996 | Mirigian et al. |
| 5,549,824 A | | 8/1996 | Trumpf et al. |
| 5,556,396 A | | 9/1996 | Cohen et al. |
| 5,562,680 A | | 10/1996 | Hasson |
| 5,570,692 A | | 11/1996 | Morinaga |
| 5,582,617 A | | 12/1996 | Klieman et al. |
| 5,588,960 A | | 12/1996 | Edwards et al. |
| 5,591,173 A | * | 1/1997 | Schifano ..................... 606/120 |
| 5,598,841 A | | 2/1997 | Taniji et al. |
| 5,614,204 A | | 3/1997 | Cochrum |
| 5,658,299 A | | 8/1997 | Hart |
| 5,662,676 A | | 9/1997 | Koninckx |
| 5,662,680 A | | 9/1997 | Desai |
| 5,665,096 A | | 9/1997 | Yoon |
| 5,672,153 A | | 9/1997 | Lax et al. |
| 5,672,172 A | | 9/1997 | Zupkas |
| 5,674,243 A | | 10/1997 | Hale |
| 5,691,314 A | | 11/1997 | Hodgen |
| 5,697,937 A | | 12/1997 | Toma |
| 5,697,942 A | | 12/1997 | Palti |
| 5,702,407 A | | 12/1997 | Kaji |
| 5,713,371 A | | 2/1998 | Sherman et al. |
| 5,713,896 A | | 2/1998 | Nardella |
| 5,713,942 A | | 2/1998 | Stern et al. |
| 5,715,832 A | | 2/1998 | Koblish et al. |
| 5,716,389 A | | 2/1998 | Walinsky et al. |
| 5,720,743 A | | 2/1998 | Bischof et al. |
| 5,749,879 A | | 5/1998 | Middleman et al. |
| 5,759,154 A | | 6/1998 | Hoyns |
| 5,766,135 A | | 6/1998 | Terwilliger |
| 5,776,129 A | | 7/1998 | Mersch |
| 5,792,059 A | | 8/1998 | Furia et al. |
| 5,797,397 A | | 8/1998 | Rosenberg |
| 5,800,378 A | | 9/1998 | Edwards et al. |
| 5,817,022 A | | 10/1998 | Vesely |
| 5,836,906 A | | 11/1998 | Edwards |
| 5,840,033 A | | 11/1998 | Takeuchi |
| 5,843,099 A | * | 12/1998 | Nichols et al. ............... 606/144 |
| 5,895,386 A | | 4/1999 | Odell et al. |
| 5,895,395 A | | 4/1999 | Yeung |
| 5,899,861 A | | 5/1999 | Friemel et al. |
| 5,904,651 A | | 5/1999 | Swanson et al. |
| 5,910,484 A | | 6/1999 | Haupert, Jr. |
| 5,911,691 A | | 6/1999 | Mochizuki et al. |
| 5,916,173 A | | 6/1999 | Kirsner |
| 5,919,206 A | * | 7/1999 | Gengler et al. ............... 606/205 |
| 5,921,933 A | | 7/1999 | Sarkis et al. |
| 5,922,008 A | | 7/1999 | Gimpelson |
| 5,941,889 A | | 8/1999 | Cermak |
| 5,979,453 A | | 11/1999 | Savage et al. |
| 6,007,552 A | * | 12/1999 | Fogarty et al. ............... 606/157 |
| 6,013,088 A | | 1/2000 | Karavidas |
| 6,015,541 A | | 1/2000 | Greff et al. |
| 6,019,724 A | | 2/2000 | Gronningsaeter et al. |
| 6,032,673 A | | 3/2000 | Savage et al. |
| 6,033,398 A | | 3/2000 | Farley et al. |
| 6,034,477 A | | 3/2000 | Peeters et al. |
| 6,035,238 A | | 3/2000 | Ingle et al. |
| 6,039,693 A | | 3/2000 | Seward et al. |
| 6,045,508 A | | 4/2000 | Hossack et al. |
| 6,066,139 A | | 5/2000 | Ryan et al. |
| 6,077,257 A | | 6/2000 | Edwards et al. |
| 6,080,118 A | | 6/2000 | Blythe |
| 6,096,051 A | | 8/2000 | Kortenbach et al. |
| 6,106,473 A | | 8/2000 | Violante et al. |
| 6,152,874 A | | 11/2000 | Looney et al. |
| 6,169,914 B1 | | 1/2001 | Hovland et al. |
| 6,175,751 B1 | | 1/2001 | Maizes |
| 6,186,947 B1 | | 2/2001 | Ouchi |
| 6,210,330 B1 | | 4/2001 | Tepper |
| 6,231,515 B1 | | 5/2001 | Moore et al. |
| 6,254,601 B1 | | 7/2001 | Burbank et al. |
| 6,261,234 B1 | | 7/2001 | Lin |
| 6,280,441 B1 | | 8/2001 | Ryan |
| 6,293,954 B1 | | 9/2001 | Fogarty et al. |
| 6,299,621 B1 | | 10/2001 | Fogarty et al. |
| 6,368,340 B2 | * | 4/2002 | Malecki et al. ............. 606/204 |
| 6,371,973 B1 | | 4/2002 | Tepper |
| 6,425,867 B1 | | 7/2002 | Vaezy et al. |
| 6,602,251 B2 | | 8/2003 | Burbank et al. |
| 6,635,017 B1 | * | 10/2003 | Moehring et al. ........... 600/439 |
| 6,692,514 B2 | * | 2/2004 | Fogarty et al. ............... 606/207 |
| 6,905,506 B2 | | 6/2005 | Burbank et al. |
| 2002/0111537 A1 | | 8/2002 | Taylor et al. |
| 2002/0165579 A1 | | 11/2002 | Burbank et al. |
| 2002/0183771 A1 | | 12/2002 | Altieri et al. |
| 2002/0188306 A1 | | 12/2002 | Burbank et al. |
| 2003/0018270 A1 | | 1/2003 | Makin et al. |

FOREIGN PATENT DOCUMENTS

| | | |
|---|---|---|
| DE | 200 22 012 U1 | 6/2001 |
| EP | 0 472 368 | 2/1992 |
| EP | 0 598 579 | 5/1994 |
| EP | 1 072 282 | 1/2001 |
| GB | 2 302 025 A | 1/1997 |
| GB | 2 311 468 A | 1/1997 |
| GB | 2302025 A * | 1/1997 |
| JP | 4-307044 | 10/1992 |
| JP | 2002-508205 | 3/2002 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | 9930623 | 6/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |

| | | |
|---|---|---|
| WO | WO 02/078521 | 10/2002 |

OTHER PUBLICATIONS

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50(7-8):337-339 (1998).

Brohim, Robert M. et al., "Development of Independent Vessel Security After Ligation With Absorbable Sutures or Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Pen-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—P roscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US03/35815 mailed Jun. 30, 2004.

International Search Report for PCT/US04/03023 mailed Feb. 9, 2005.

International Search Report for PCT/US04/01935 mailed Feb. 15, 2005.

International Search Report for PCT/US2004/038276, mailed Mar. 15, 2005.

International Preliminary Report of Patentability for Serial No. PCT/US04/01935, mailed Jul. 8, 2005.

Garza Leal, J. et al., "Myoma Treatment by Transient Uterine Ischemia", *The Journal of the American Association of Gynecologic Laparoscopists* 7(3):S31 (Aug. 2000).

\* cited by examiner

VASCULAR CLAMP FOR CAESARIAN SECTION

FIELD OF THE INVENTION

The invention relates generally to the field of treatment of diseases and conditions by the regulation of blood flow in blood vessels. In particular, the invention is directed to the treatment of uterine hemorrhage by reducing blood flow in a uterine artery.

BACKGROUND OF THE INVENTION

Delivery of a baby is followed by separation of the placenta from the uterine wall, usually resulting in a significant loss of blood. Fortunately, the uterus is resistant to anoxic damage caused by reduced blood flow. For example, uterine muscle is typically poorly perfused during labor contractions, yet typically suffers no lasting ill effects from this situation. However, hemorrhage from the uterus following delivery may cause loss of a significant fraction of the mother's blood if it is not stopped quickly. Blood loss from prolonged hemorrhage following delivery presents a serious threat to the life and health of the mother.

The muscular contractions and hormonal changes accompanying vaginal delivery promote rapid cessation of postpartum hemorrhage. However, caesarian delivery is typically not accompanied by such contractions and hormonal changes, and also entails physical injury to the uterus additional to that caused by placental separation. Delivery by caesarian section is thus often accompanied by hemorrhage from the placental attachment site and from the uterine incision required for delivery of the infant. Medical intervention is typically required to reduce blood loss following caesarian deliveries.

The primary blood supply to the uterus, both in the non-gravid uterus and in the pregnant uterus, is from the uterine arteries. A small communicating artery arising from each ovarian artery reaches uterus but in gravid and non-gravis states supplies less than 10% of uterine blood flow. The uterine arteries arise from the internal iliac arteries and reach the uterus through the base of the broad ligament in a space that can not be seen from a surgical perspective looking down on the uterus from within the peritoneal cavity or from a gynecological perspective looking up at the cervix from the vagina. The uterine arteries are, therefore, not visible.

Once the uterine arteries reach the uterus, they give rise to a large ascending branch that supplies the uterus and a smaller descending branch that supplies the cervix. These branches, in turn, give rise to anterior and posterior arcuate arteries. Right and left anterior arcuate arteries anastomose in the anterior sagittal midline of the uterus; posterior arcuate arteries, in the posterior sagittal uterine midline. Consequently, to reduce blood loss following caesarian delivery from the hysterotomy site and from the placenta attachment site, right and left uterine arteries must both be occluded.

Attempts have been made to reduce caesarian delivery blood loss. One method has been to initiate uterine contractions by administering oxytocin or oxytocin-like drugs following caesarian delivery. Another method has been blind clamping of the uterine and ovarian arteries using rubber covered arterial clamps, which was proposed as early as 1922. Similarly, intestinal clamps have been applied to the uterus along its right and left lateral borders, across the entire broad ligament, to minimize caesarian blood loss. Another method includes bilateral surgical ligation of the internal iliac arteries to diminish hemorrhage following caesarian delivery. Bilateral surgical ligation of the uterine arteries, or of the ascending branches of the uterine arteries, to reduce hemorrhaging has been performed from abdominal cavity and from transvaginal approaches. Intravascular balloon occlusion of the aorta and embolic occlusion of the uterine arteries have also been used to treat caesarian hemorrhage. However, all of these methods have met with only limited adoption for a variety of reasons.

For example, many physicians do not possess the training or equipment necessary to perform catheter-based uterine artery embolization under radiologic direction. In addition, such treatments are not appropriate in the case of caesarian hemorrhage, where rapid treatment can be critical and arterial catheterization may not be practical.

Location of the uterine arteries in a patient immediately following a caesarian delivery may be difficult; in addition to being located within the broad ligament that supports the uterus, the uterine arteries are near or within the caesarian surgical field, and so are typically covered with blood, amniotic fluid, and the like which can impede visual identification and medical access following caesarian section. Rapid identification and location of the uterine arteries is required in order to prevent unchecked hemorrhage.

Accordingly, there is need for devices and methods to control blood flow in blood vessels such as uterine arteries by physicians with little training in a simple medical setting or environment.

SUMMARY OF THE INVENTION

This invention is directed to therapeutic procedures which include occluding a target vessel with a clamping device having a pair of opposed pressure-applying members with facing pressure-applying surfaces configured to grasp a patient's tissue. At least one of the pressure-applying members have a yieldable and preferably resilient pressure-applying surface which contacts tissue. As used herein the terms "yieldable" and "resilient" or words of similar import refer to being yieldable or resilient under the conditions of use. The invention is particularly suitable for occluding a patient's uterine artery after a caesarian delivery.

The pressure-applying surfaces yield with pressure upon contact with tissue, so that the surface moves, or is deformed, or compresses upon contact with tissue and application of pressure to tissue. Such surfaces may be resilient, in that they at least partially recover their original configuration or position following release of pressure. The pressure applying surface or surfaces attached to the pressure-applying members of the clamping device can be pressed against the target vessel such as a uterine artery to be occluded or against a tissue bundle containing the target vessel to be occluded in order to partially or completely stop blood flow through the target vessel. The procedure and the instruments for such procedure are suitable for occluding an artery such as a uterine artery to prevent or at least minimize blood loss during a surgical procedure. The procedure is particularly suitable to partially or completely occlude a female patient's uterine or ovarian artery during a caesarian delivery.

In one embodiment of the invention, at least one of the pressure-applying surfaces is provided with a sensor to locate the blood vessel and may be used to detect the reduction or termination of blood flow through an occluded or partially occluded blood vessel during the procedure. A particularly suitable sensor mounted on the yielding pressure-applying surface attached to the pressure-applying member is an ultrasonic based Doppler sensor operating at a frequency of about 5 to about 20 MHz, preferably about 6 to about 10 MHz.

The yieldably (e.g., movably, compressibly, or otherwise giving in response to pressure) and preferably resiliently mounted pressure-applying surface can be applied to tissue to facilitate location of a blood vessel to be occluded without applying a significant clamping force on the blood vessel which can significantly affect blood flow through the blood vessel. Once the blood vessel is located by a sensor on the one or more pressure-applying surfaces, more pressure may be applied to the one or more pressure-applying surfaces to partially or totally occlude the blood vessel. The distance between the opposed pressure-applying members is adjustable, by, for example, the pressure-applying members being connected by a pivot and able to rotate around it effective to apply adequate pressure to tissue.

The pressure-applying surfaces may themselves be yieldable or resilient surfaces. In addition, or alternatively, the pressure-applying surfaces may be joined with the pressure-applying members by a yieldable connection, preferably configured to allow transverse motion of the pressure-applying surface with respect to its supporting pressure-applying member. In preferred embodiments, the yieldable connection joining the pressure-applying surfaces with the pressure-applying members comprises a resilient connection. In this way, the pressure-applying surfaces provide a floating jaw attached to the pressure-applying members by a yieldable, and preferably resilient, connection. Such a floating jaw is configured to engage tissue and to lightly contact tissue with minimal pressure to locate the blood vessel, and, upon application of greater amounts of force that more fully compress the yieldable or resilient connection, to apply pressure to tissue sufficient to occlude a blood vessel within or adjacent the contacted tissue.

The sensors suitable for use with the clamping devices of the invention are preferably blood flow sensors, more preferably Doppler ultrasound blood flow sensors, and may be a sensor/transducer. A Doppler sensor may provide audible identification of an artery; for example, a Doppler sensor with a sensor controller having a speaker may provide audible identification of the uterine arteries through the broad ligament without the need for tissue dissection in the broad ligament and visual identification of the blood vessel. The sensor may be a sensor/transducer including a source of energy, or may be a passive sensor, responding to energy supplied externally of the sensor.

Each of the pressure applying members of the clamping device embodying features of the invention preferably has a handle which are pivotally connected. The proximal ends of the handles may include a locking mechanism such as ratcheting mechanisms to lock the pressure applying members in a closed or partially closed condition. Preferably, the locking mechanism is releasable so at the completion of the procedure the clamping device may be removed from the patient.

An arterial clamp embodying features of the invention is useful for sensing the location of a uterine artery within or adjacent the broad ligament secured to the uterus, and is useful to compress and occlude a uterine artery within the broad ligament.

One method of occluding an artery comprises clamping the artery effective to compress it so that blood flow through the vessel is reduced, or is abolished. Arterial occlusion is temporary, being relieved after removal of the device, and may be partial or complete.

A controller may be provided for the blood flow sensor to aid in detecting the location of a uterine artery, by generating a signal related to the output of the sensor that can be readily used by an operator. The sensor controller may also include an energy source for the blood flow sensor, such as a source of ultrasound energy, electrical energy, or electromagnetic energy. The energy may be directly provided by the energy source or may be provided by the sensor with the aid of the energy source.

Utilization of the clamping device having features of the invention to occlude a uterine artery following a caesarian delivery can prevent excessive blood loss and importantly with such prevention of blood loss, allows increased time for improved suturing of the uterus. For example, a two- or three-layer surgical closure can be performed without the worries of excessive bleeding. This can affect better closure with less complication from incisions or scarring of the uterus which can lead to abortions or uterine rupture during future pregnancies.

The devices, systems and methods embodying features of the invention may be effectively used with little or no training. These and other advantages of the invention will become more apparent from the following detailed description of the invention when taken in conjunction with the accompanying exemplary drawings.

DETAILED DESCRIPTION OF THE INVENTION

Figure 1:
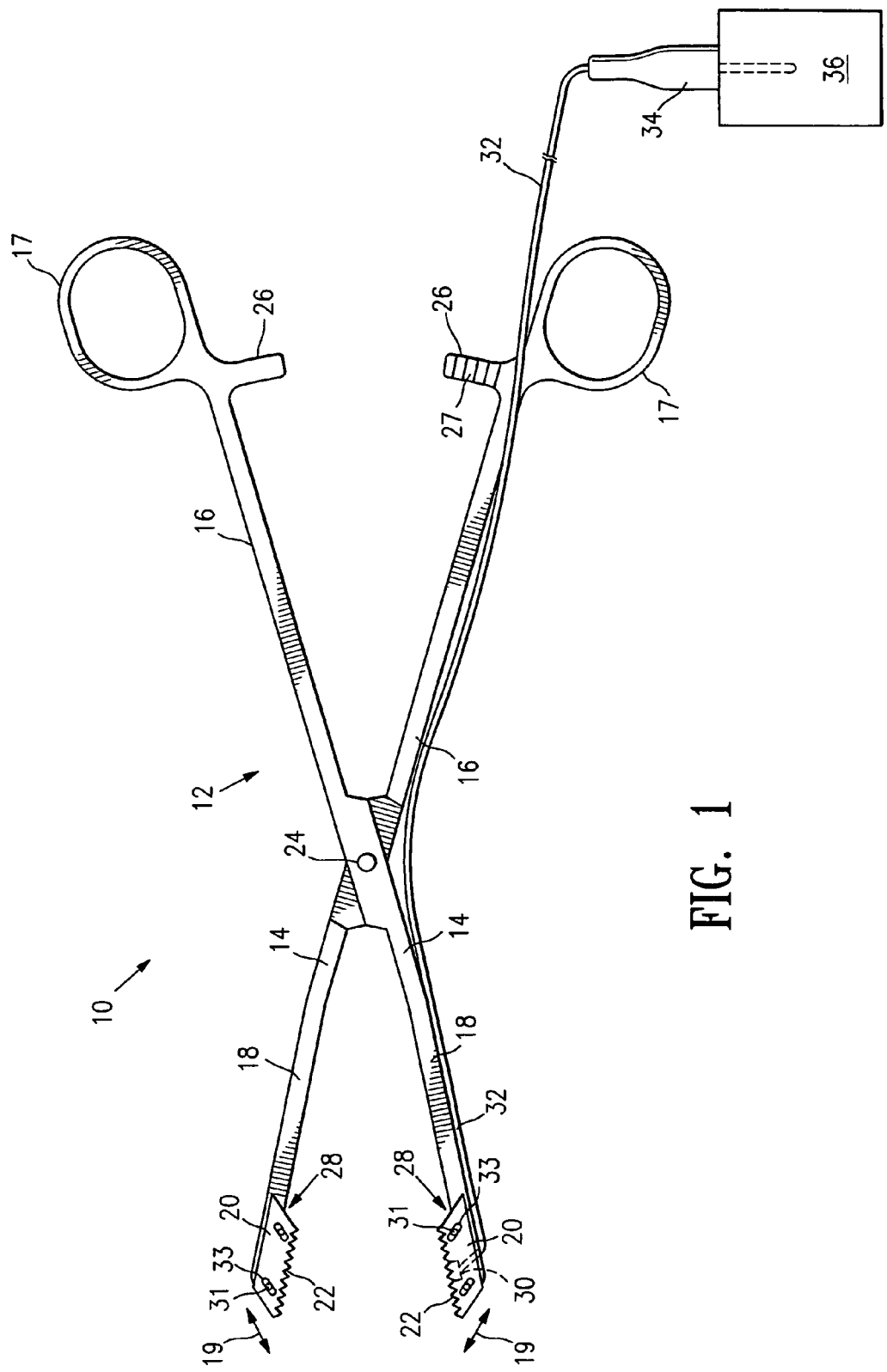
FIG. 1 is a plan view of a blood vessel occluding system including an arterial clamp embodying features of the invention which is disposed in an open configuration.

FIGS. 1-4 show a uterine artery-occluding system 10 embodying features of the invention which includes a clamping device 12 having clamping members 14, handles 16 with finger grips 17, pressure-applying members 18 and floating jaws 20 on the pressure applying members. Floating jaws 20 have serrated pressure-applying surfaces 22 configured to engage and hold onto tissue when floating jaws 20 are pressed into a patient's body tissue. Clamping members 14 are pivotally interconnected at pivot point 24. Clamping members 14 are preferably formed with the handles 16 integral with the pressure applying members 18. The operator squeezes the finger grips 17 on clamping members 14 to cause pressure-applying surfaces 22 to approach one another as the separation distance between pressure-applying members 18 decreases. Each of the handles 16 are provided with releasable locking mechanism 26 including two complementary ratchet portions 27 configured to engage with each other and to lock clamping members 14 in a closed or partially closed position, maintaining pressure or force between pressure-applying surfaces 22 while the locking mechanism 26 is engaged.

Floating jaws 20 are movably joined to pressure-applying members 18 by a connection 28. Connection 28 is a yieldable connection, so that pressure on pressure-applying surface 22, or contact with a surface by pressure-applying surface 22 while pressure is applied by pressure-applying members 18, causes motion of a floating jaw 20 with respect to a pressure-applying member 18 as shown by the arrows 19. Thus, closure of pressure-applying surface 22 onto a surface affected by movement of pressure-applying arm 18 causes motion of a floating jaw 20 with respect to a pressure-applying member 18 so as to decrease the separation between the pressure-applying surface 22 and the pressure-applying member 18. A yieldable connection 28 provides a floating jaw 20 with a range of motion with respect to a pressure-applying member 18 with little or no pressure on tissue initially but increased pressure as the floating jaw 20 collapses onto the pressure applying member 18.

Yieldable connection 28 is preferably a resilient connection, so that compression is met with some resistance to such compression and so connection 28 at least partially resumes its original configuration upon release of compression. For example, where connection 28 is a resilient connection, movement of floating jaw 20 with respect to a pressure-applying member 18 is met with resistance when movement of pressure-applying arm 18 presses pressure-applying surface 22 onto tissue. A resilient connection may be provided by a spring, rubber, elastic, or other resilient material or members disposed between a pressure-applying member 18 and floating jaw 20. Following relief of pressure on a resilient yieldable connection 28, the separation between the pressure-applying surface 22 and the pressure-applying member 18 increases.

Artery-occluding system 10 also includes a sensor or sensor means 30 and an energy transmitting member or means such as an electrical conductor 32. The conductor 32 has a proximal connector 34 configured to operably engage with sensor controller 36. Sensor 30 is configured to sense the location a uterine artery and generate a signal representing the location which provides an output representing the signal received from the sensor. Preferably, the sensor 30 also to determine the degree of occlusion of the uterine artery after clamping the device on the artery or tissue containing the artery and generates a signal representing such occlusion which the controller 36 also converts to an output representative thereof. Sensor 30, preferably a Doppler ultrasound sensor, is connected via an electrical conductor 32 and connector 34 configured to readily engage and disengage with a Doppler ultrasound controller 36. Alternatively, the proximal end of cable 32 may directly and permanently engage or be secured to the sensor control device 36 without having a connector 34.

The sensor controller 36 is configured to supply power required by a sensor 30, to receive signals from a sensor 30, and to provide sensor signal outputs for interpretation by an operator. In addition, sensor controller 36 may produce signals or signal energy used for sensing (e.g., ultrasound or infra-red signals or energy) or may provide energy to a sensor 30 to aid the sensor 30 to produce or provide signals or signal energy.

FIGS. 2A-2D illustrate a distal part of system 10 embodying features of the invention, showing a variety of resilient members 29. Yieldable connection 28 joins pressure-applying surface 22 to pressure-applying member 18, and is preferably configured to allow a range of movement of the pressure-applying surface 22 with respect to its supporting pressure-applying member 18 as indicated by the arrows 19. Light pressure between a pressure-applying surface 22 and body tissue, such as a uterine artery or tissue adjacent or surrounding a uterine artery, is effective to cause movement of a pressure-applying surface 22 towards a pressure-applying member 18 as a pressure-applying member 18 urges a pressure-applying surface 22 towards body tissue. However, yieldable connection 28 compresses under such light pressure, at least during an initial application of light pressure, allowing pressure-applying surface 22 to move relative to pressure-applying member 18 so as to contact tissue without substantially compressing the tissue. The yieldable, preferably resilient connection 28 is thus effective to maintain contact between the pressure-applying surface 22 and tissue under the influence of light pressure from the pressure-applying members 18 without substantially compressing the artery and without occluding it. This allows for utilization of the sensor to locate the blood vessel without interfering with blood flow through the blood vessel.

Figure 2A:
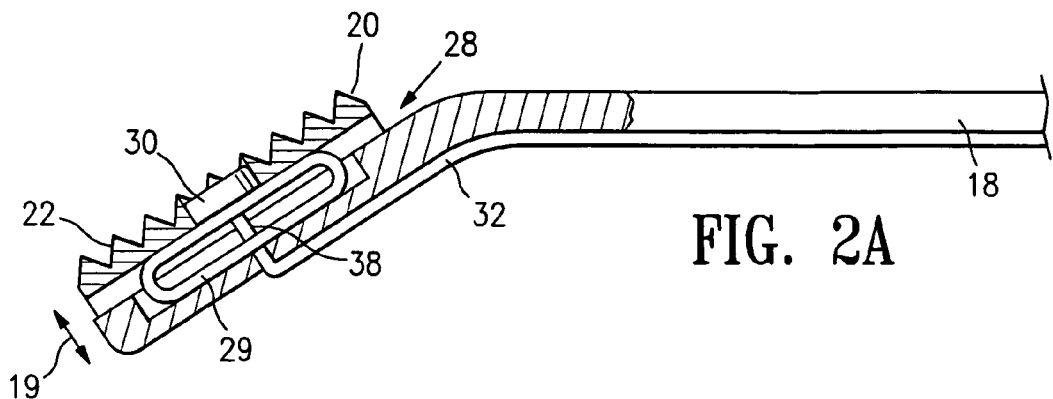
FIG. 2A is a fragmentary sectional view of a distal portion of an arterial clamp embodying features of the invention having a pressure applying member with an "O"-ring providing resiliency.

In the embodiments illustrated in FIGS. 2A-2D, a yieldable connection 28 includes a resilient member 29 compressed between pressure-applying member 18 and floating jaw 20. In preferred embodiments, for example, as illustrated in FIG. 2A, resilient member or compressible means 29 comprises an "O"-ring compressed between a pressure-applying means or member 18 and a floating tissue-contacting means or jaw 20. Floating jaw 20 is constrained to move substantially only in a single direction by pins 31 attached to pressure-applying member 18 and disposed within slots 33 in lateral sides 35 of floating jaw 20. Alternatively, a pressure-applying member 18 may have slots configured to receive pins attached to a floating jaw 20.

Figure 2B:
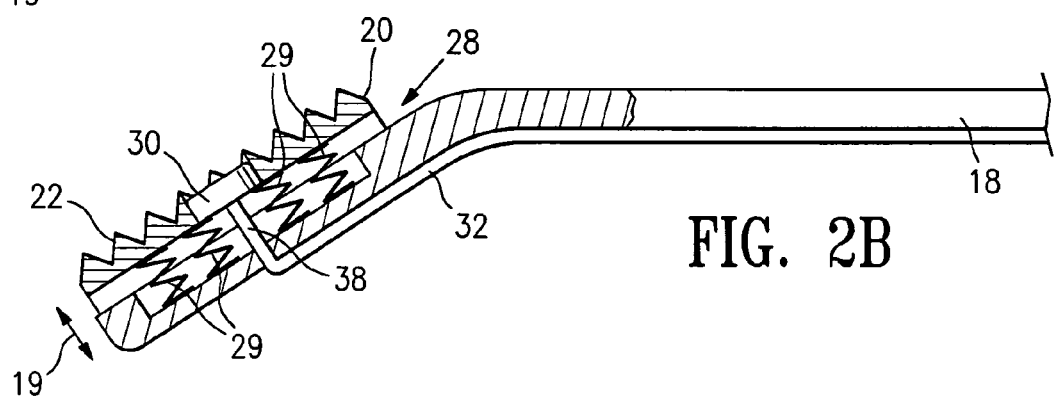
FIG. 2B is a fragmentary sectional view of a distal portion of an arterial clamp embodying features of the invention having a pressure applying member with a plurality of springs providing resiliency.
Figure 2C:
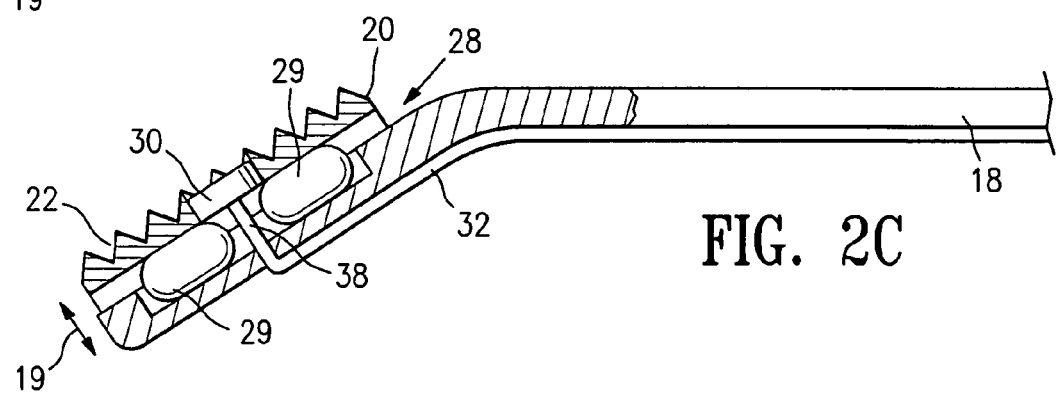
FIG. 2C is a fragmentary sectional view of a distal portion of an arterial clamp embodying features of the invention having a pressure applying member with a flexible bladder to provide resiliency.
Figure 2D:
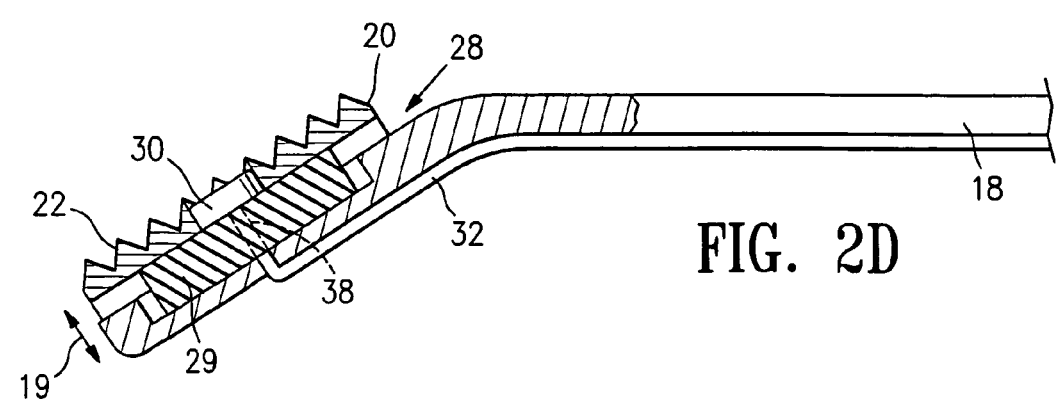
FIG. 2D is a fragmentary sectional view of a distal portion of an arterial clamp embodying features of the invention having a pressure applying member with an elastic layer providing resiliency.

As illustrated in FIG. 2B, resilient members 29 are springs, which may be coil springs, leaf springs, or other springs. In FIG. 2C, the resilient member 29 shown is a flexible bladder filled with a compressible fluid such as a gas. In FIG. 2D, the resilient member 29 shown is a layer formed of resilient material placed between pressure-applying member 18 and floating jaw 20. A resilient member 29 can be formed of an elastic material (e.g., silicone rubber, latex, or other rubber or elastomer, a sponge or spongy material).

In the embodiments shown in FIG. 2A-2D, floating jaws 20 meet pressure-applying members 18 at an angle, unlike the embodiment shown in FIG. 1 where floating jaws 20 meet pressure-applying members 18 to form approximately straight angles. It will be understood that floating jaws 20 may be disposed at any suitable angle with respect to pressure-applying members 18 to accommodate a variety of anatomical conditions.

A sensor 30 may be disposed on a pressure-applying member 18, a floating jaw 20, or other distal portion of a clamping device 12. The sensor 30 for locating a uterine artery, including a sensor for measuring blood flow, is preferably disposed in or on a pressure-applying member 18, and is preferably mounted to the face of a pressure-applying surface 22, such as the face of a floating jaw 20 of a clamping device 12. Clamping devices 12 embodying features of the invention may include more than one blood flow sensor 30.

By providing a blood flow sensor on at least one of the yieldable, and preferably resilient pressure application members, they may be disposed proximate to the patient's uterine artery to maintain contact with the tissue without occluding the artery, and thereby readily sense blood flow therein and thereby locate the uterine artery. Increasing pressure on pressure-applying surface 22 provides better contact between sensor 30 and tissue, but within the compressible range of motion of yieldable connection 28, the partial clamping of the device does not occlude a blood vessel. Further increase in pressure on pressure-applying surface 22, so as to compress yieldable connection 28 near to or to its limit of motion, is effective to apply the pressure directly to the tissue and so to occlude an artery within or near the contacted tissue. The sensor 30 may then be employed to monitor blood flow through the artery and thereby follow the occlusion of the artery.

A clamping member 14 is preferably configured for manipulating a pressure-applying member 18. In some embodiments of devices 12 having features of the invention, a pressure-applying member 18 is attached to a connecting portion that is configured so that a pressure-applying member 18 or pressure-applying surface 22 may be placed on or adjacent an artery while a handle 16 is distally disposed and available for use by an operator.

Bringing clamping members 14 together is effective to dispose pressure-applying surfaces 22 in close apposition to one another. In this way, with clamping device 12 placed near to tissue, pressure-applying surfaces 22 may be placed in contact with tissue disposed between floating jaws 20, such as a portion of a uterine artery. Partial or complete closure of floating jaws 20 causes pressure-applying surfaces 22 to apply pressure or force to the tissue effective to compress a uterine artery or the tissue around a uterine artery; the application of pressure or force is effective to compress the tissue and to occlude the uterine artery, reducing or abolishing blood flow through at least a portion of the uterine artery.

A sensor 30 disposed on a floating jaw 20 is also shown in each of FIGS. 2A-2D, with a portion of conductor 32 shown disposed along a portion of a pressure-applying member 18. A sensor 30 is effective to detect the location of an artery within tissue adjacent a pressure-applying surface 22. For example, placement of a sensor 30 disposed on or in a pressure-applying surface 22 onto a broad ligament containing a uterine artery is effective to detect blood flow in a uterine artery. Such detection is useful in order to direct the placement of a system 10 so as to ensure that body tissue including a portion of a uterine artery to be occluded is between floating jaws 20 of the clamping device 12. In preferred methods of use, the uterine artery and surrounding tissue is disposed between floating jaws 20 and pressure or force is applied to the tissue by pressure-applying surfaces 22, applying pressure to the tissue, effective to compress a portion of a uterine artery and to at least partially occlude the uterine artery. Such compression and resulting occlusion of a uterine artery is effective to reduce or abolish blood flow in the vessel. Sensor 30, disposed on floating jaws 20, is effective to sense the reduction or abolition of blood flow in a compressed uterine artery.

Figure 3:
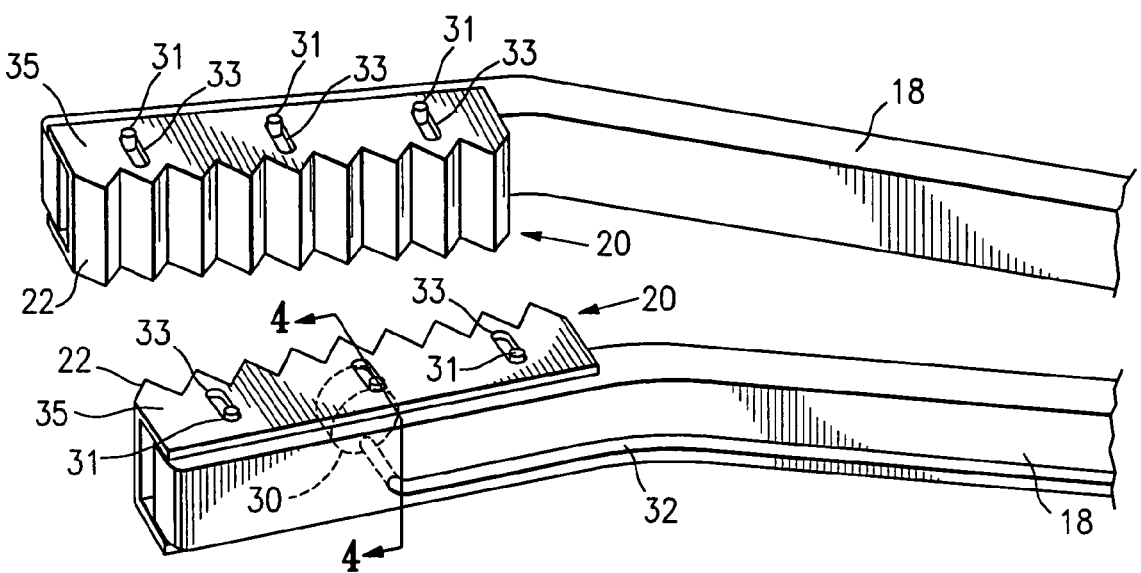
FIG. 3 is a perspective view of an angled distal portion of an arterial clamp embodying features of the invention disposed in an open configuration.

FIG. 3 illustrates in greater detail the distal portion of clamping device 12 having pressure-applying members 18 with floating jaws 20 having pressure-applying surfaces 22. A sensor 30 is shown disposed on a jaw 20 on the pressure-applying surface 22, with a distal portion of a cable 32 disposed opposite the pressure-applying surface 22.

Figure 4:
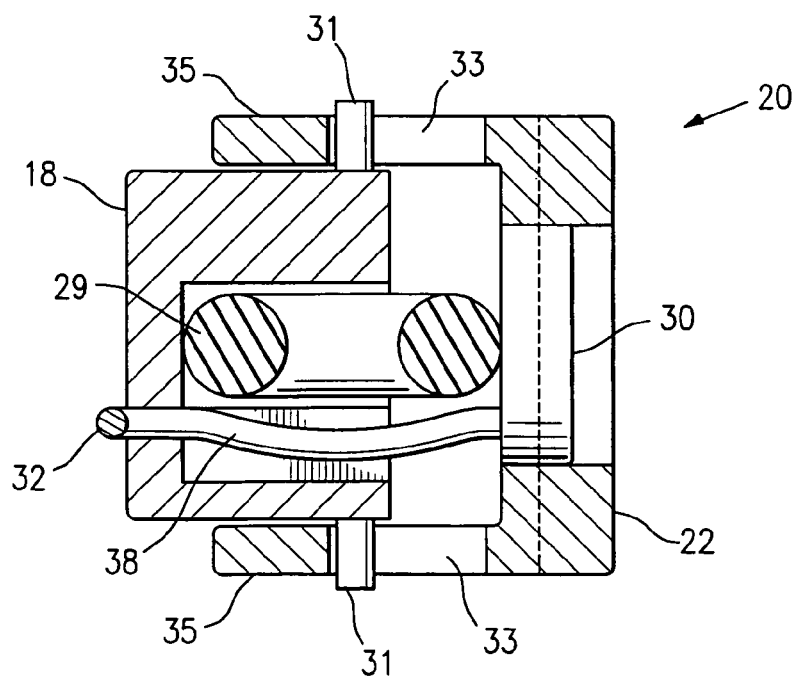
FIG. 4 is a transverse cross-sectional view of one jaw of the angled distal portion of the clamping device of FIG. 3 taken at line 4-4.

FIG. 4 is a cross-sectional view of a jaw 20, taken through a sensor 30 along line 4-4 of FIG. 3 illustrating movement of floating jaw 20 with respect to pressure-applying surface 22. Such movement is allowed by pin 31 slidably received within slot 33 in lateral side 35 of floating jaw 20. However, movement of floating jaw 20 in other directions is constrained by pin 31 slidably received within slot 33 in lateral side 35 of floating jaw 20. Resilient member 29 shown in FIG. 4 is an "O"-ring.

Sensor 30 is connected with conductor 32 by connection 38, shown in the figure as a wire. In alternative embodiments, a connection 38 may comprise a plurality of wires, an optical fiber or fibers, a waveguide, or other connection effective to carry signals and/or energy or power between a sensor 30, a conductor 32, and a sensor controller 36. Preferably, connection 38 is a continuation of at least a portion of conductor 32. Connection 38 is preferably configured to accommodate transverse movement of sensor 30 disposed within floating jaw 20, and thus is preferably a flexible or slidable connection. Alternatively, a sensor 30 may be disposed on a pressure-applying member 18 and a floating jaw 20 configured to permit operation of sensor 30 through or around pressure-applying surface 22. For example, a floating jaw 20 may include a portion transparent to sensing energy, a passage, a window, or other feature allowing operation of a sensor 30.

A sensor 30 is termed a passive sensor where it is configured to detect intrinsic signals indicating the presence of a uterine artery (i.e., a sound sensor, a pressure sensor, a motion sensor, a pH sensor, or other sensor configured to detect a physical, chemical, electrical, or physiological indication of the location of a uterine artery). A sensor 30 is an active sensor where it is configured to emit a signal, and to detect a signal in response to, or derived from, the emitted signal. An emitted signal may be pulsed or continuous. In alternative embodiments, for example where a sensor 30 senses an optical or electromagnetic signal, conductor 32 may include an optical fiber, a waveguide, other conduit for carrying energy or signals, or a combination of these. A sensor 30 is preferably an active sensor.

A sensor 30 that produces, at least in part, the energy used to produce the signal sensed by the sensor (i.e., an active sensor) may be called a sensor/transducer. A sensor/transducer may have a source of ultrasound and an ultrasound sensor or a source of infrared radiation and an infrared detector. For example, an infrared blood-flow sensor is sensitive to electromagnetic energy having a wavelength of between about 500 nanometers (nm) and about 2000 nm, preferably between about 700 nm and about 1000 nm.

A sensor 30 is preferably a Doppler ultrasound sensor. A Doppler ultrasound sensor operating at ultrasound frequencies less than or equal to about 20 MHz, such as between about 5 MHz and about 20 MHz, preferably between about 6 MHz and about 10 MHz. a typical frequency of about 8 Hz, is suitable for detecting blood flow in an artery with apparatus embodying features of the invention.

The operation of a sensor may be aided by an energy source (e.g., provided by a sensor controller 36), which may directly provide the energy detected by the sensor, or which may aid the sensor to provide the energy to be sensed. For example, an energy source may provide electrical energy which aids an ultrasound sensor to produce and to detect ultrasound energy (as, e.g., in the MedaSonics® CardioBeat® Blood Flow Doppler with Integrated Speaker (Cooper Surgical, Inc., Trumbull Conn. 06611)). Other commercially available Doppler ultrasound sensors suitable for use in the present invention include the Koven model ES 100×MiniDop VRP-8 probe (St. Louis, Mo.) and the DWL/Neuro Scan Medical Systems' Multi-Dop B+ system (Sterling, Va.).

When used to reduce uterine hemorrhage following caesarian section, a clamping device 12 having features of the invention must close the uterine artery within the broad ligament and stay in-place to maintain closure of the vessel. In preferred embodiments, a clamping device 12 having features of the invention is configured so as to allow an operator to "feel" the broad alignment during placement to allow contact by the Doppler chip without premature closure of the uterine artery. Light pressure of the pressure-applying surfaces 22 onto tissue such as the broad ligament, allows detection of blood flow in an artery (e.g., the uterine artery) without occluding it. Resilient connection 28 maintains the light pressure with tissue, and allows an operator to readily probe multiple locations during detection of a target artery. The resilient connection 28 aids in audible identification of the uterine artery within a broad ligament by allowing an operator to press a clamping device 12 into tissue sufficiently to sense blood flow without occluding it.

Closure of a uterine artery may be partial or total. Sufficient pressure or force applied to tissue is effective to apply pressure to that tissue and to underlying tissues and so to compress and to at least partially occlude a uterine artery. An amount of pressure applied to effect closure of a uterine artery may be between about 1 pound per square inch (psi) and about 60 psi, and may preferably be between about 3 psi and about 30 psi. For example, where the pressure-applying surface has a surface area of about 0.16 square inches (e.g., a surface with dimensions of about 0.2 inches by about 0.8 inches), the amount of force applied by an artery occluding device embodying features of the invention is preferably between about 0.2 pounds and about 10 pounds, and more preferably between about 0.6 pounds and about 5 pounds.

A sensor 30 may detect a uterine artery, or blood flow, or signals related to the location of a uterine artery or of blood flow, in a particular direction. For example, a sensor 30 disposed on a pressure-applying surface 22 of a floating jaw 20 may detect signals from a direction perpendicular to the surface, and so be effective to locate uterine arteries or detect blood flow opposite the floating jaw 20. Such an orientation is effective to insure that a uterine artery to be occluded is positioned opposite a floating jaw 20, and between a pair of floating jaws 20, and so is properly placed for occlusion. A sensor 30 may also be configured to detect signals from directions parallel to a pressure-applying surface 22, or at some other angle with respect to a pressure-applying surface 22; such configurations are useful, for example, for directing the movement of a clamping device 12 towards a uterine artery.

A clamping device 12 embodying features of the invention may be configured to lock into a clamping position. Such a locked configuration may be temporary and releasable, or may be permanent. Clamping devices 12 embodying features of the invention may have a locking mechanism 26, such as a ratchet, configured to hold at least one pressure-applying member 18 in a pressure-applying position. Such locking mechanisms 26 should include a release mechanism effective to allow the cessation of pressure or force application when desired.

The apparatus and systems of the present invention are configured for use within a patient's body cavity. The dimensions of a clamping device 12 embodying features of the invention are chosen to facilitate use within the surgical field after caesarian section, so that the clamping device 12 may readily reach, detect and occlude a uterine artery when manipulated by an operator's hand or hands. Clamping devices 12 may be of any suitable size consistent with such a preferred use, and may also be determined in part by the location and dimension of the artery to be occluded. For example, a clamping device 12 configured to allow access to tissue adjacent a uterine artery and to apply pressure or force to the tissue sufficient to reduce or abolish blood flow in the uterine artery may be between about 1 inch and about 12 inches in length, preferably between about 3 inches and about 8 inches in length.

A sensor is preferably mounted to and oriented perpendicularly to the pressure-applying surface 22 of a floating jaw 20. For example, a blood flow sensor may be mounted between about 0.1 inch and about 1 inch from the distal end of a floating jaw 20, and is preferably mounted about 0.1 inch to about 0.6 inch, more preferably about 0.3 inch to about 0.5 inch from the distal tip of a floating jaw 20. A floating jaw 20 may be configured to tightly engage tissue, i.e., may have a tissue contacting surface 22 that is serrated, scored, roughened, coated with a rough material including sandpaper, or otherwise configured to grip tissue.

Figure 5:
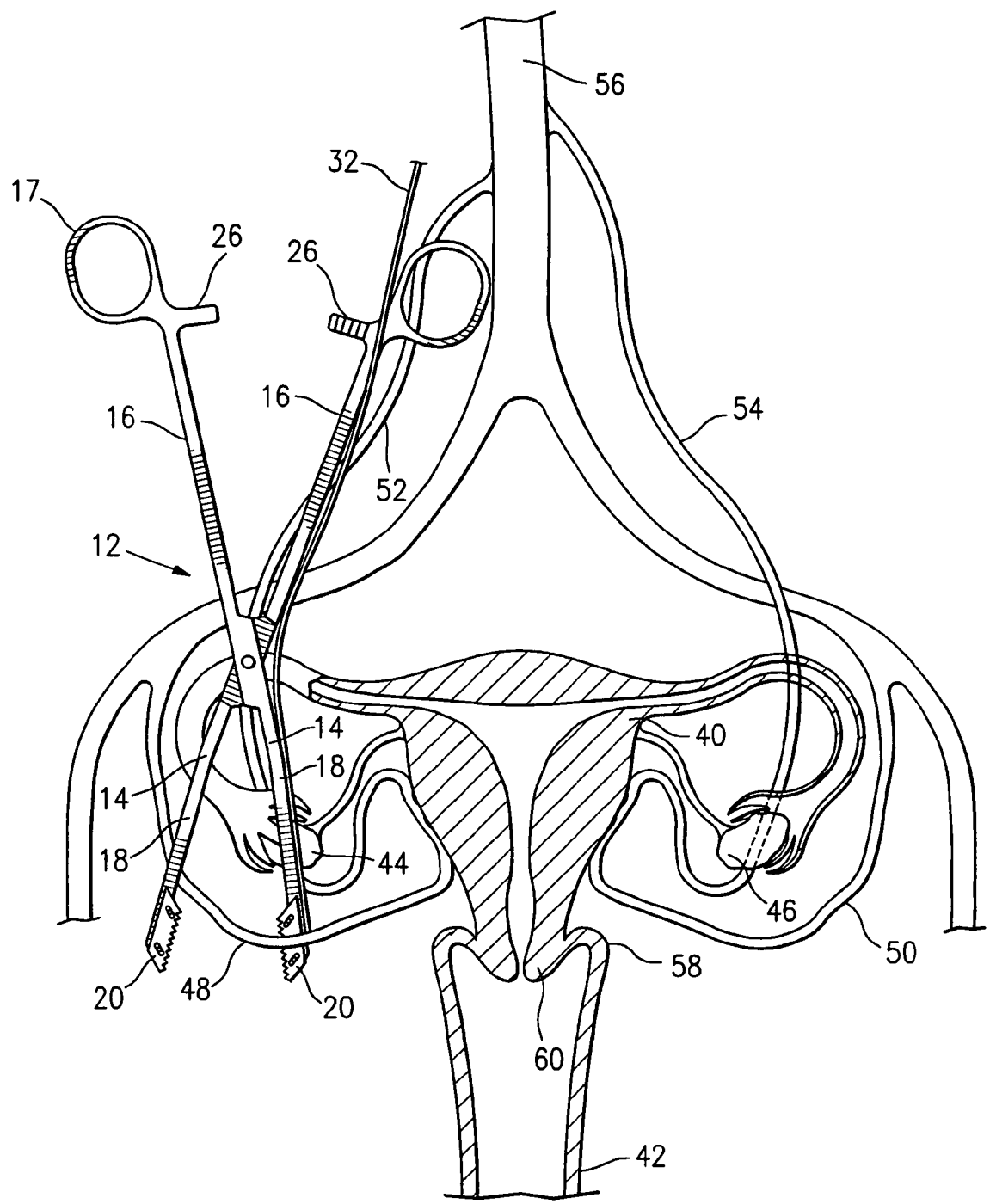
FIG. 5 is schematic diagram of a reproductive system of a human female including major uterine arteries providing blood flow to the uterus showing the deployment of the arterial clamp shown in FIG. 1 in a female patient's anatomy.

It will be understood that methods and devices embodying features of the invention may be used to occlude a variety of arteries; but is particularly suitable for occluding a uterine artery. FIG. 5 illustrates a typical human female reproductive system, including a uterus 40, vagina 42, right ovary 44, and left ovary 46. Blood is supplied to the uterus 40 primarily via the right uterine artery 48 and the left uterine artery 50, and secondarily via the right ovarian artery 52 and the left ovarian artery 54, all of which are supplied by the aorta 56. Uterine arteries 48 and 50 contact the uterus 40 and pass near to the vaginal fornix 58 and to the uterine cervix 60.

At least a portion of the uterus 40 is exposed and made accessible to a physician during caesarian section. The uterine arteries 48 and 50 may also be made accessible by the surgical procedures necessary for performing a caesarian delivery. However, even if this does not occur during the normal course of the operation, the uterine arteries 48 and 50 may readily be accessed by a physician during or following delivery of the baby and placenta. Tissue near a uterine artery, such as broad ligament tissue, or, where the broad ligament has been dissected away over at least a portion of a uterine artery, uterine artery tissue, may be contacted by a clamping device having features of the invention when a physician determines that occlusion of one or both uterine arteries is indicated. Typically, this would not occur until after delivery of the baby and the clamping of the umbilical cord, and, in most cases, also after cutting the umbilical cord and after separation of the placenta from the uterus.

Placement of a pressure-applying surface 22 having a sensor 30, such as a pressure-applying surface 22 of a floating jaw 20 with a sensor 30 such as a Doppler ultrasound sensor, against tissue allows a physician to locate a uterine artery 48 or 50 despite visual obstructions such as blood, amniotic fluid, tissue, and other impediments to locating an artery in a caesarian-section patient. A yieldable connection 28 (preferably a resilient yieldable connection 28) joining floating jaw 20 with a pressure-applying member 18 allows for initially light contact between a device 12 and tissue. A yieldable connection 28 allows effective contact between sensor 30 and tissue to provide blood flow sensing without substantial occlusion of blood flow. Thus, pressure applied by pressure-applying members 18 keeps pressure-applying surface 22 and sensor 30 in contact with tissue without applying such pressure as would occlude a uterine artery 48 or 50 during the location process. It may be desirable to observe blood flow in a uterine artery 48 or 50 for a period of time before occluding it. For example, blood flow in a uterine artery 48 or 50 may be observed with a sensor 30 at different locations to determine an optimal location for occlusion; in addition, such observation of blood flow over time may allow a physician to determine when to begin applying pressure to occlude a uterine artery 48 or 50, or whether such occlusion is indicated under the circumstances. Application of increased pressure is effective to occlude a uterine artery 48 or 50. Increased pressure applied by pressure-applying members 18 is effective to compress a yieldable connection 28 near to or to the limit of its range of motion and to compress tissue in contact with a pressure-applying surface 22.

Thus, a method of occluding a blood vessel includes contacting tissue with a pressure-applying surface 22 of a device 12 and locating a blood vessel within or adjacent the tissue without occluding blood flow in it, and compressing the tissue with the device 12 to occlude blood flow in the blood vessel.

A method of occluding an artery of a patient includes contacting tissue near an artery, without substantially compressing the artery, with a pressure-applying surface of a clamping device having features of the invention. A sensor disposed on the pressure-applying surface is effective to locate the artery. At least a portion of the artery may be compressed by applying pressure to tissue adjacent the artery with the clamping device. Compressing an artery may include grasping tissue near to an artery, and may include compressing tissue surrounding an artery effective to compress the artery. Compressing tissue with an artery occluding device is preferably effective to compress the artery so that blood flow through the artery is reduced, or is abolished. A method of occluding a uterine artery would thus comprise this method, where the artery was a uterine artery.

FIG. 5 illustrates the use of an artery occluding device embodying features of the invention to occlude blood flow in a uterine artery 48. A clamping device 12 with clamping members 14, handles 16, and pressure-applying members 18 with floating jaws 20 having pressure-applying surfaces 22 is shown in place within the abdominal cavity of a patient after delivery of an infant by caesarian section. A clamping device 12 is shown with floating jaws 20 having pressure-applying surfaces 22 disposed on tissue around a uterine artery 48. The clamping device 12 also includes a sensor 30 on a floating jaw 20 facing the patient's tissue, and communicating with other parts of the system 10 (not shown in FIG. 5) via a cable 32.

Compressing a uterine artery may be accomplished by compressing a portion of the broad ligament around a portion of a uterine artery 48 or 50, or by compression via direct contact between the device and a uterine artery 48 or 50. As illustrated in FIG. 5, sensor 30 is effective to detect the presence of and to locate uterine artery 48, and to detect blood flow in the artery 48. Sensor 30 is used to aid in positioning floating jaws 20 and pressure-applying surfaces 22 to best surround uterine artery 48. Closing floating jaws 20 presses pressure-applying surfaces 22 more strongly into tissue, compressing uterine artery 48 effective to occlude uterine artery 48. Sensor 30 may be used to detect the resulting reduction or abolition of blood flow in uterine artery 48, and to adjust the amount of pressure or force used in order to provide the desired amount of reduction in blood flow and to confirm abolition of blood flow if desired. Locking mechanism 26 is used to maintain the desired amount of pressure or force on the tissue for a desired amount of time. Blood flow in the left uterine artery 50 may be similarly occluded, by the same clamping device 12 (after release of the occlusion of the right uterine artery 48) or by a different clamping device 12 (thus allowing simultaneous clamping and occlusion of both uterine arteries).

Clamping devices 12 embodying features of the invention may be made from any suitable material or combination of materials, including metals such as stainless steel and shape memory alloys such as nickel titanium alloys, plastics, ceramics, and other materials known in the art. Biocompatible polymers, such as for example, polycarbonate, polysulfone, polyester, polyacetal, and other polymers may be particularly suitable for embodiments of the invention. The device or system may be designed for single use (disposable) or may be sterilizable and capable of multiple use.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention be defined by the scope of the appended claims as broadly as the prior art will permit, and in view of the specification if need be. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

What is claimed is:

1. An arterial clamping system comprising:
    a. a clamping device for at least partially occluding a target vessel in a patient's body, comprising a pair of opposed pressure-applying members configured to at least partially occlude the target vessel by applying pressure thereto, with at least one of the pressure-applying members having a floating, pressure-applying jaw with a continuous pressure applying surface movably mounted thereto and having a resilient connection between the floating, pressure-applying jaw and the pressure applying member, the resilient connection being at least partially surrounded by side walls extending from the continuous pressure applying surface of the floating, pressure-applying jaw and toward the pressure-applying member, wherein the side walls have a plurality of slots and the at least one of the pressure-applying members has a plurality of pins projecting from lateral edges thereof that are disposed in the slots for guiding movement of said floating, pressure-applying jaw; and a sensor on at least one of the pressure-applying jaws for locating the target vessel, wherein the sensor is movably mounted to a distal end of the clamping device; and
    b. a sensor controller operatively connected to the sensor and comprising a source of power.

2. The system of claim 1, wherein the sensor comprises a Doppler ultrasound sensor and the sensor controller comprises a Doppler ultrasound controller.

3. The system of claim 1, wherein the side walls extend from the pressure-applying surface of the floating, pressure applying jaw and are slideable over the lateral edges of the pressure-applying member.

4. The system of claim 1, wherein the sensor is flexibly connected with the clamping device for being movable relative to a distal end of the clamping device.

5. The system of claim 1, wherein the sensor is connected with the pressure-applying jaw for moving with the pressure-applying jaw and is movable relative to a distal end of the at least one of the pressure-applying members.

6. A device for treating a female patient's uterus after caesarian section by occluding the patient's uterine artery comprising:

a pair of opposed clamping elements having pressure-applying jaws configured to at least partially occlude a target uterine artery by applying pressure thereto;

at least one of the pressure-applying jaws being a floating jaw movably mounted to one of the clamping elements and having a resilient connection with the one of the clamping elements; and a blood flow sensor disposed on at least one of the pressure applying jaws for locating the target uterine artery to be clamped, wherein the floating jaw has side walls extending from a clamping surface thereof, the side walls being slideable over lateral edges of the one of the clamping elements, wherein the opposed side walls of the floating jaw have slots that receive pins projecting from the lateral edges of the one of the clamping elements.

7. The device of claim 6, wherein the pins are slideable in the slots for guiding movement of a continuous pressure applying surface of the floating jaw toward and away from the one of the clamping elements.

8. The device of claim 6, wherein the blood flow sensor is connected with the floating jaw for moving with the floating jaw, and wherein the blood flow sensor is movable relative to a distal end of the one of the clamping elements.

9. A device for treating a female patient's uterus by occluding a uterine artery thereof comprising:

a pair of opposed clamping elements;

at least one of the clamping elements having a floating pressure-applying jaw movably mounted thereto, wherein the jaw includes a continuous pressure-applying surface and is adapted to at least partially occlude a target uterine artery by applying pressure thereto;

a resilient connection between the clamping element and the jaw movably mounted thereto, the resilient connection being at least partially surrounded by side walls extending between the continuous pressure-applying surface of the floating pressure-applying jaw and one of the opposed clamping elements;

a guide assembly coupled with the floating pressure-applying jaw for guiding movement of the floating pressure-applying jaw toward and away from the at least one of the opposed clamping elements; and a blood flow sensor disposed on at least one of the pressure applying jaws for locating the target uterine artery to be clamped, wherein the blood flow sensor is attached to the floating pressure-applying jaw for moving with the floating pressure-applying jaw, wherein the floating pressure-applying jaw comprises opposing side walls extending from the continuous pressure-applying surface thereof to lateral edges of the at least one of the clamping elements, wherein the guide assembly comprises slots formed in the opposing side walls of the floating pressure-applying jaw and pins projecting from the lateral edges of the at least one of the clamping elements, and wherein the slots receive the pins.

10. The clamping device of claim 9, wherein the blood flow sensor comprises sensor/transducer means for providing signals and for sensing reflected signals for locating the target uterine artery.

11. The clamping device of claim 9 wherein each of the clamping elements has an elongated handle.

12. The clamping device of claim 11 wherein the handles of the clamping elements are pivotally secured together.

13. The system of claim 9, wherein the pins are slideable in the slots for guiding movement of the continuous pressure applying surface of the floating pressure-applying jaw toward and away from the at least one of the clamping elements.

14. The system of claim 9, wherein the blood flow sensor is flexibly connected with the device for being movable relative to a distal end of the device.

15. A clamping device for occluding a target vessel comprising:

a pair of opposed pressure-applying members;

at least one of said pressure-applying members having a distal end including a yieldable pressure-applying surface;

a guide assembly coupled with the at least one of said pressure-applying members for guiding movement of said yieldable pressure-applying surface toward and away from the at least one of said pressure applying members;

further comprising a floating jaw coupled with the at least one of said pressure-applying members, wherein said floating jaw includes said yieldable pressure-applying surface wherein said floating jaw is mounted over an inner face of the at least one of said pressure-applying members, wherein said floating jaw includes side walls extending from said yieldable pressure-applying surface toward the at least one of said pressure-applying members associated therewith, wherein said guide assembly comprises slots formed in each of said side walls of said floating jaw, and wherein said slots in each of said side walls are parallel with one another and extend away from said yieldable pressure-applying surface.

16. The clamping device as claimed in claim 15, wherein said guide assembly constrains movement of said yieldable pressure-applying surface in a single direction relative to the at least one of said pressure applying members associated therewith.

17. The clamping device as claimed in claim 15, wherein said guide assembly further comprises pins projecting from lateral edges of the at least one of said pressure-applying members, and wherein said pins are disposed in said slots in each of said side walls of said floating jaw for guiding movement of said floating jaw in a single direction.

18. The clamping device as claimed in claim 17, wherein said side walls extending from said pressure-applying surface of said floating jaw are slideable over said lateral edges of said pressure-applying member.

19. The clamping device as claimed in claim 18, wherein said pins are slideable in said slots for guiding movement of said floating jaw relative to the at least one of said pressure-applying members.

20. The clamping device as claimed in claim 15, wherein said slots extend along axes that are substantially perpendicular to said yieldable pressure-applying surface of said floating jaw.

21. The clamping device as claimed in claim 15, further comprising a resilient connection between said floating jaw and the inner face of the at least one of said pressure-applying members for normally urging said yieldable pressure-applying surface away from the inner face of the at least one of said opposed pressure-applying members.

22. The clamping device as claimed in claim 21, wherein said resilient connection is a resilient connection selected from the group consisting of springs, O-rings, hydraulic connections, compressed gas connections, and resilient members.

23. The clamping device as claimed in claim 21, wherein the inner face of the at least one of said pressure-applying members has a recess formed therein, and wherein a part of said resilient connection is seated within the recess.

24. The clamping device as claimed in claim 15, further comprising a sensor on at least one of said opposed pressure-applying members for locating a vessel.

25. The clamping device as claimed in claim 24, wherein said yieldable pressure-applying surface defines an area, and wherein said sensor is substantially centered within the area of said yieldable pressure-applying surface.

26. The clamping device of claim 24, wherein said sensor is a Doppler ultrasound sensor.

27. The clamping device of claim 15, wherein each of said pressure-applying members has a floating jaw movable mounted thereto with a resilient connection between said pressure applying member and said floating jaw.

* * * * *

UNITED STATES PATENT AND TRADEMARK OFFICE
CERTIFICATE OF CORRECTION

PATENT NO. : 7,651,511 B2  Page 1 of 1
APPLICATION NO. : 10/359386
DATED : January 26, 2010
INVENTOR(S) : Burbank et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Twenty-eighth Day of December, 2010

David J. Kappos
*Director of the United States Patent and Trademark Office*